(12) United States Patent
Rohde et al.

(10) Patent No.: US 11,400,193 B2
(45) Date of Patent: Aug. 2, 2022

(54) IN-LINE SENSORS FOR DIALYSIS APPLICATIONS

(71) Applicants: BAXTER INTERNATIONAL INC., Deerfield, IL (US); BAXTER HEALTHCARE S.A., Glattpark (CH)

(72) Inventors: Justin B. Rohde, Des Plaines, IL (US); William Wenli Han, Long Grove, IL (US); Elizabeth A. Everitt, Libertyville, IL (US); Michael Edward Hogard, Odessa, FL (US); Ying-Cheng Lo, Green Oaks, IL (US); Erin Michele Copeland, Bradford, PA (US); William Patrick Burns, Channahon, IL (US)

(73) Assignees: Baxter International Inc., Deerfield, IL (US); Baxter Healthcare SA

( * ) Notice: Subject to any disclaimer, the term of this patent is extended or adjusted under 35 U.S.C. 154(b) by 629 days.

(21) Appl. No.: 15/941,278

(22) Filed: Mar. 30, 2018

(65) Prior Publication Data

US 2018/0221555 A1 Aug. 9, 2018

Related U.S. Application Data

(62) Division of application No. 12/200,488, filed on Aug. 28, 2008, now abandoned.

(51) Int. Cl.
*A61M 1/16* (2006.01)
*A61M 1/28* (2006.01)

(52) U.S. Cl.
CPC .......... *A61M 1/1656* (2013.01); *A61M 1/166* (2014.02); *A61M 1/1607* (2014.02);
(Continued)

(58) Field of Classification Search
CPC .... A61M 1/14; A61M 1/1601; A61M 1/1603; A61M 1/1605; A61M 1/1607;
(Continued)

(56) References Cited

U.S. PATENT DOCUMENTS 2,122,509 A 7/1938 Beliaeff
2,529,028 A 11/1950 Landon
(Continued)

FOREIGN PATENT DOCUMENTS

CN 1897993 1/2007
CN 2905076 5/2007
(Continued)

OTHER PUBLICATIONS

Prime Faraday Partnership, "An Introduction to MEMS," Wolfson School of Mechanical and Manufacturing Engineering Loughborough University, Loughborough, Leics LE11 3TU (2002), 56 pages. (Year: 2002).*

(Continued)

*Primary Examiner* — Pranav N Patel
(74) *Attorney, Agent, or Firm* — K&L Gates LLP

(57) ABSTRACT

A system for monitoring water quality for dialysis, dialysis fluids, and body fluids treated by dialysis fluids, is disclosed. The system uses microelectromechanical systems (MEMS) sensors for detecting impurities in input water or dialysis fluid, and in the prepared dialysate. These sensors may also be used to monitor and check the blood of the patient being treated. These sensors include ion-selective sensors, for ions such as ammonium or calcium, and also include amperometric array sensors, suitable for ions from chlorine or chloramines, e.g., chloride. These sensors assist in the monitoring of water supplies from a city water main or well.

(Continued)

The sensors may be used in conjunction with systems for preparing dialysate solutions from water for use at home or elsewhere.

19 Claims, 6 Drawing Sheets

(52) U.S. Cl.
CPC ........ *A61M 1/1674* (2014.02); *A61M 1/1696* (2013.01); *A61M 1/28* (2013.01); *A61M 1/287* (2013.01)

(58) Field of Classification Search
CPC .............. A61M 1/1609; A61M 1/1617; A61M 1/1619; A61M 1/1654; A61M 1/1656; A61M 1/166; A61M 1/1675; A61M 1/1694; A61M 1/1696; A61M 1/28; A61M 1/287; A61M 2205/70; A61M 2205/702; A61M 2205/3306; A61M 2205/3324; A61M 2205/3327; A61M 2205/3331; A61M 2205/3368; A61M 2205/3379; G01N 35/00; G01N 35/00584; G01N 35/00594; G01N 35/00712; G01N 35/00613; G01N 35/00663; G01N 35/11673; G01N 35/00603; G01N 35/08; G01N 2035/00178; G01N 29/02; G01N 29/022
See application file for complete search history.

(56) References Cited

U.S. PATENT DOCUMENTS

| | | |
|---|---|---|
| 3,332,737 A | 7/1967 | Krause |
| 3,388,803 A | 6/1968 | Scott |
| 3,463,728 A | 8/1969 | Kolobow et al. |
| 3,485,245 A | 12/1969 | Lahr et al. |
| 3,490,479 A | 1/1970 | Mott et al. |
| 3,528,550 A | 9/1970 | Cappelen, Jr. |
| 3,545,438 A | 12/1970 | De Vries |
| 3,608,729 A | 9/1971 | Leeds |
| 3,617,545 A | 11/1971 | Dubois et al. |
| 3,619,423 A | 11/1971 | Galletti et al. |
| 3,667,612 A | 6/1972 | Leonard |
| 3,669,878 A | 6/1972 | Marantz et al. |
| 3,669,880 A | 6/1972 | Marantz et al. |
| 3,682,817 A | 8/1972 | Marx |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,799,873 A | 3/1974 | Brown |
| 3,809,241 A | 5/1974 | Alvine |
| 3,825,493 A | 7/1974 | Brown et al. |
| 3,827,975 A | 8/1974 | Bizot et al. |
| 3,850,835 A | 11/1974 | Marantz et al. |
| 3,878,564 A | 4/1975 | Yao et al. |
| 3,884,808 A | 5/1975 | Scott |
| 3,911,915 A | 10/1975 | Seifter et al. |
| 3,926,797 A | 12/1975 | Gigou et al. |
| 3,939,069 A | 2/1976 | Granger et al. |
| 3,979,284 A | 9/1976 | Granger et al. |
| 3,989,622 A | 11/1976 | Marantz et al. |
| 4,000,072 A | 12/1976 | Sato et al. |
| 4,031,010 A | 6/1977 | Nose |
| 4,036,747 A | 7/1977 | Hori et al. |
| 4,081,372 A | 3/1978 | Atkin et al. |
| 4,115,259 A | 9/1978 | Bigi |
| 4,118,314 A | 10/1978 | Yoshida |
| 4,173,537 A | 11/1979 | Newhart et al. |
| 4,180,460 A | 12/1979 | Calar |
| 4,190,047 A | 2/1980 | Jacobsen et al. |
| 4,191,646 A | 3/1980 | Larsson et al. |
| 4,192,748 A | 3/1980 | Hyden |
| 4,194,536 A | 3/1980 | Stine et al. |
| 4,212,738 A | 7/1980 | Henne |
| 4,213,859 A | 7/1980 | Smakman et al. |
| 4,240,408 A | 12/1980 | Schael |
| 4,247,393 A | 1/1981 | Wallace |
| 4,256,718 A | 3/1981 | McArthur et al. |
| 4,267,040 A | 5/1981 | Schal |
| 4,267,047 A | 5/1981 | Henne et al. |
| 4,269,708 A | 5/1981 | Bonomini et al. |
| 4,276,175 A | 6/1981 | Bower |
| 4,293,762 A | 10/1981 | Ogawa |
| 4,303,521 A | 12/1981 | Lehmann |
| 4,313,831 A | 2/1982 | Lehmann et al. |
| 4,338,190 A | 7/1982 | Kraus et al. |
| 4,360,507 A | 11/1982 | McArthur et al. |
| 4,364,747 A | 12/1982 | Blackshear et al. |
| 4,381,003 A | 4/1983 | Buoncristiani |
| 4,399,036 A * | 8/1983 | Babb ................... A61M 1/1656 210/638 |
| 4,460,555 A | 7/1984 | Thompson |
| 4,464,563 A | 8/1984 | Jewett |
| 4,473,449 A | 9/1984 | Michaels et al. |
| 4,498,900 A | 2/1985 | Buoncristiani |
| 4,532,414 A | 7/1985 | Shah et al. |
| 4,542,015 A | 9/1985 | Smakman et al. |
| 4,581,141 A | 4/1986 | Ash |
| 4,586,920 A | 5/1986 | Peabody |
| 4,618,343 A | 10/1986 | Polaschegg |
| RE32,303 E | 12/1986 | Lasker et al. |
| 4,650,857 A | 3/1987 | May |
| 4,661,246 A | 4/1987 | Ash |
| 4,678,460 A | 7/1987 | Rosner |
| 4,680,445 A | 7/1987 | Ogawa |
| 4,684,460 A | 8/1987 | Issautier |
| 4,702,829 A | 10/1987 | Polaschegg et al. |
| 4,703,913 A | 11/1987 | Hunkapiller |
| 4,718,890 A | 1/1988 | Peabody |
| 4,735,609 A | 4/1988 | Comeau et al. |
| 4,747,822 A | 5/1988 | Peabody |
| 4,765,907 A | 8/1988 | Scott |
| 4,769,151 A | 9/1988 | Shouldice |
| 4,804,474 A | 2/1989 | Blum |
| 4,844,074 A | 7/1989 | Kurucz |
| 4,846,950 A | 7/1989 | Yao et al. |
| 4,847,470 A | 7/1989 | Bakke |
| 4,906,816 A | 3/1990 | van Leerdam |
| 4,950,259 A | 8/1990 | Geary et al. |
| 4,976,683 A | 12/1990 | Gauthier et al. |
| 5,004,459 A | 4/1991 | Peabody et al. |
| 5,073,167 A | 12/1991 | Carr et al. |
| 5,125,069 A | 6/1992 | O'Boyle |
| 5,141,492 A | 8/1992 | Dadson et al. |
| 5,141,493 A | 8/1992 | Jacobsen et al. |
| 5,180,896 A | 1/1993 | Gibby et al. |
| 5,227,820 A | 7/1993 | Miyashita et al. |
| 5,245,693 A | 9/1993 | Ford et al. |
| 5,252,213 A * | 10/1993 | Ahmad ................. A61M 1/169 210/542 |
| 5,277,820 A | 1/1994 | Ash |
| 5,284,470 A | 2/1994 | Beltz |
| 5,336,173 A | 8/1994 | Folden |
| 5,338,293 A | 8/1994 | Jeppsson et al. |
| 5,350,357 A | 9/1994 | Kamen et al. |
| 5,366,630 A | 11/1994 | Chevallet |
| 5,370,674 A | 12/1994 | Farrell |
| 5,381,510 A | 1/1995 | Ford et al. |
| 5,408,576 A | 4/1995 | Bishop |
| 5,420,962 A | 5/1995 | Bakke |
| 5,438,510 A | 8/1995 | Bryant et al. |
| 5,470,483 A | 11/1995 | Bene et al. |
| 5,474,683 A | 12/1995 | Bryant et al. |
| 5,486,286 A * | 1/1996 | Peterson ............. A61M 1/1686 210/87 |
| 5,498,338 A | 3/1996 | Kruger et al. |
| 5,522,998 A | 6/1996 | Polaschegg |
| 5,542,919 A | 8/1996 | Simon et al. |
| 5,631,025 A | 5/1997 | Shockley et al. |

(56) References Cited

U.S. PATENT DOCUMENTS

| | | |
|---|---|---|
| 5,641,405 A | 6/1997 | Keshaviah et al. |
| 5,643,201 A | 7/1997 | Peabody et al. |
| 5,645,734 A | 7/1997 | Kenley et al. |
| 5,674,404 A * | 10/1997 | Kenley ............... A61L 2/04 |
| | | 210/741 |
| 5,683,381 A | 11/1997 | Carr et al. |
| 5,685,988 A | 11/1997 | Malchesky |
| 5,685,989 A | 11/1997 | Krivitski et al. |
| 5,690,614 A | 11/1997 | Carr et al. |
| 5,690,821 A | 11/1997 | Kenley et al. |
| 5,722,947 A | 3/1998 | Jeppsson et al. |
| 5,724,478 A | 3/1998 | Thweatt |
| 5,729,653 A | 3/1998 | Magliochetti et al. |
| 5,744,042 A | 4/1998 | Stange et al. |
| 5,762,782 A | 6/1998 | Kenley et al. |
| 5,774,042 A | 6/1998 | Johnston |
| 5,776,091 A | 7/1998 | Brugger et al. |
| 5,790,752 A | 8/1998 | Anglin et al. |
| 5,816,779 A | 10/1998 | Lawless et al. |
| 5,836,908 A | 11/1998 | Beden et al. |
| 5,858,238 A | 1/1999 | McRea et al. |
| 5,873,853 A | 2/1999 | Keilman et al. |
| 5,875,282 A | 2/1999 | Jordan et al. |
| 5,876,611 A | 3/1999 | Shettigar |
| 5,902,336 A | 5/1999 | Mishkin |
| 5,919,369 A | 7/1999 | Ash |
| 5,921,951 A | 7/1999 | Morris |
| 5,938,634 A | 8/1999 | Packard |
| 5,944,684 A | 8/1999 | Roberts et al. |
| 5,960,160 A | 9/1999 | Clark et al. |
| 5,980,481 A | 11/1999 | Gorsuch |
| 5,984,891 A | 11/1999 | Keilman et al. |
| 5,989,238 A | 11/1999 | Ginsburg |
| 5,989,423 A | 11/1999 | Kamen et al. |
| 6,042,784 A | 3/2000 | Wamsiedler et al. |
| 6,069,343 A | 5/2000 | Kolowich |
| 6,074,359 A | 6/2000 | Keshaviah et al. |
| 6,091,976 A | 7/2000 | Pfeiffer et al. |
| 6,129,699 A | 10/2000 | Haight et al. |
| 6,139,528 A | 10/2000 | Kistner et al. |
| 6,142,974 A | 11/2000 | Kistner et al. |
| 6,142,975 A | 11/2000 | Jalisi et al. |
| 6,146,359 A | 11/2000 | Carr et al. |
| 6,146,536 A | 11/2000 | Twardowski |
| 6,168,578 B1 | 1/2001 | Diamond |
| 6,175,688 B1 | 1/2001 | Cassidy et al. |
| 6,193,684 B1 | 2/2001 | Burbank et al. |
| 6,196,992 B1 | 3/2001 | Keilman et al. |
| 6,210,361 B1 | 4/2001 | Kamen et al. |
| 6,220,299 B1 | 4/2001 | Arvidsson et al. |
| 6,228,047 B1 | 5/2001 | Dadson |
| 6,229,957 B1 | 5/2001 | Baker |
| 6,234,991 B1 | 5/2001 | Gorsuch |
| 6,234,992 B1 | 5/2001 | Haight et al. |
| 6,236,809 B1 | 5/2001 | Cassidy et al. |
| 6,245,039 B1 | 6/2001 | Brugger et al. |
| 6,254,567 B1 | 7/2001 | Treu et al. |
| 6,261,261 B1 | 7/2001 | Gordon |
| 6,261,809 B1 | 7/2001 | Bertling et al. |
| 6,274,103 B1 * | 8/2001 | Taylor ................ C02F 1/444 |
| | | 422/261 |
| 6,290,669 B1 | 9/2001 | Zicherman |
| 6,293,921 B1 | 9/2001 | Shinmoto et al. |
| 6,302,653 B1 | 10/2001 | Bryant et al. |
| 6,323,182 B1 | 11/2001 | Linden et al. |
| 6,409,699 B1 | 6/2002 | Ash |
| 6,579,253 B1 | 6/2003 | Burbank et al. |
| 6,602,502 B1 | 8/2003 | Strahilevitz |
| 6,666,842 B1 | 12/2003 | Sakai |
| 6,746,607 B1 | 6/2004 | Vijayalakshmi et al. |
| 6,812,031 B1 | 11/2004 | Carlsson |
| 6,861,033 B2 | 3/2005 | Mullins et al. |
| 6,960,179 B2 | 11/2005 | Gura |
| 6,960,322 B2 | 11/2005 | Stringer et al. |
| 7,100,427 B2 | 9/2006 | Kahn et al. |
| 7,104,115 B2 | 9/2006 | Kahn et al. |
| 7,189,314 B1 | 3/2007 | Pace et al. |
| 7,241,272 B2 | 7/2007 | Karoor et al. |
| 7,249,000 B2 | 7/2007 | Kahn et al. |
| 7,867,214 B2 | 1/2011 | Childers et al. |
| 7,922,686 B2 | 4/2011 | Childers et al. |
| 2001/0027289 A1 | 10/2001 | Treu et al. |
| 2001/0037079 A1 | 11/2001 | Burbank et al. |
| 2001/0041873 A1 | 11/2001 | Dopper et al. |
| 2001/0041892 A1 | 11/2001 | Burbank et al. |
| 2002/0088875 A1 | 7/2002 | Balschat et al. |
| 2002/0147423 A1 | 10/2002 | Burbank et al. |
| 2002/0187940 A1 | 12/2002 | Masuda et al. |
| 2003/0000876 A1 | 1/2003 | Kawaguchi |
| 2003/0105424 A1 | 6/2003 | Karoor et al. |
| 2004/0019312 A1* | 1/2004 | Childers ............... A61M 1/288 |
| | | 604/4.01 |
| 2004/0019313 A1* | 1/2004 | Childers ............... A61M 1/28 |
| | | 604/5.01 |
| 2004/0079686 A1 | 4/2004 | Moscaritolo et al. |
| 2004/0082903 A1 | 4/2004 | Micheli |
| 2005/0082226 A1* | 4/2005 | Bene ............... A61M 1/3656 |
| | | 210/646 |
| 2005/0101901 A1 | 5/2005 | Gura |
| 2005/0102028 A1 | 5/2005 | Amin et al. |
| 2005/0131331 A1 | 6/2005 | Kelly et al. |
| 2005/0131332 A1 | 6/2005 | Kelly et al. |
| 2005/0251366 A1 | 11/2005 | Kahn et al. |
| 2006/0020427 A1 | 1/2006 | Kahn et al. |
| 2006/0277977 A1 | 12/2006 | Kahn et al. |
| 2007/0007184 A1 | 1/2007 | Voto et al. |
| 2007/0050157 A1 | 3/2007 | Kahn et al. |
| 2007/0079686 A1 | 4/2007 | Hsieh |
| 2007/0179431 A1 | 8/2007 | Roberts et al. |
| 2007/0219728 A1 | 9/2007 | Papageorgiou et al. |
| 2008/0011664 A1 | 1/2008 | Karoor et al. |
| 2008/0021381 A1 | 1/2008 | Lurvey et al. |
| 2008/0109175 A1 | 5/2008 | Michalak |

FOREIGN PATENT DOCUMENTS

| | | |
|---|---|---|
| CN | 200961108 | 10/2007 |
| DE | 19828923 | 1/2000 |
| DE | 19814695 | 9/2001 |
| EP | 64393 | 11/1982 |
| EP | 152717 | 8/1985 |
| EP | 402505 | 12/1993 |
| EP | 498382 | 11/1996 |
| EP | 778033 | 11/1996 |
| EP | 575512 | 5/1998 |
| EP | 928615 | 7/1999 |
| EP | 956876 | 11/1999 |
| EP | 980685 | 2/2000 |
| EP | 659092 | 10/2000 |
| EP | 847769 | 8/2001 |
| EP | 243547 | 7/2011 |
| GB | 2122509 | 1/1984 |
| GB | 2124511 | 2/1984 |
| JP | 92002060 | 1/1992 |
| JP | 4348757 | 12/1992 |
| JP | 07299455 | 11/1995 |
| JP | 8029224 | 2/1996 |
| JP | 9327511 | 12/1997 |
| JP | 10085324 | 4/1998 |
| JP | 11137672 | 5/1999 |
| JP | 2002-35113 | 2/2005 |
| JP | 2005-144389 | 6/2005 |
| JP | 2007-29939 | 2/2007 |
| SU | 1012918 | 3/1981 |
| SU | 1344362 | 6/1984 |
| WO | 9420158 | 9/1994 |
| WO | 9502559 | 1/1995 |
| WO | 9535124 | 12/1995 |
| WO | 9747337 | 6/1997 |
| WO | 9817333 | 4/1998 |
| WO | 9903519 | 1/1999 |
| WO | 9906082 | 2/1999 |
| WO | 0020050 | 4/2000 |
| WO | 0020052 | 4/2000 |

(56) References Cited

FOREIGN PATENT DOCUMENTS

| WO | 0050143 | 8/2000 |
|----|---------|--------|
| WO | 0057928 | 10/2000 |
| WO | 02/066099 | 8/2002 |
| WO | 2004009158 | 1/2004 |
| WO | 2006074429 | 11/2004 |
| WO | 2005/044339 | 5/2005 |
| WO | 2007027843 | 3/2007 |

OTHER PUBLICATIONS

Office Action for Japanese Patent Application No. 2011-525031 dated Jul. 24, 2013.
U.S. Appl. No. 15/195,801, filed Jun. 28, 2016.
"Fresnius 90/2 Peritoneal Therapy Cylcer" Article, written by Fresenius USA, dated Jul. 1993.
Office Action for Japanese Application No. 2011-525031 dated Jul. 18, 2014.
Denial of Entry of Amendment for Japanese Application No. 2011-525031 dated Jul. 18, 2014.
Office Action for Chinese Application No. 200980133542.3 dated Sep. 1, 2014.
Office Action for Chinese Application No. 200980133542.3 dated Feb. 19, 2014.
Office Action for Japanese Patent Application No. 2011-525031 dated Dec. 13, 2013.
Office Action for Mexican Application No. MX/a/2011/002196 dated Apr. 23, 2014.
Office Action for Canadian Application No. 2,733,511 dated May 20, 2015.
Office Action for Mexican Patent Application No. MX/a/2011/002196 dated Jul. 15, 2013.
Office Action for Chinese Patent Application No. 200980133542.3 dated May 29, 2013.

\* cited by examiner

IN-LINE SENSORS FOR DIALYSIS APPLICATIONS

PRIORITY

This application claims priority to and the benefit as a divisional application of U.S. patent application Ser. No. 12/200,488, filed Aug. 28, 2008, entitled, "In-Line Sensors for Dialysis Applications", the entire contents of which are incorporated herein by reference and relied upon.

BACKGROUND

This patent relates generally to medical fluid delivery systems and methods. More particularly, this patent discloses systems, methods and apparatuses for microelectromechanical systems (MEMS) sensors for sensing and measuring species in fluids involved in dialysis, such as peritoneal dialysis fluid, hemodialysis fluid, and blood.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters or needles are inserted into the patient's veins and arteries, or an artificial graft so blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, referred to as dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" may occur at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems may clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to monitor and control the composition of the dialysis fluid, including the water used to make the dialysis fluid. The purity of the incoming water is obviously important. In home situations, there is typically no control or monitoring of the water from a city main or from a person's well. Once the dialysis fluid is made, it may be useful to at least check its complete composition, at least to insure that the proper fluid is being used. At present this cannot be done without taking a sample to a lab for testing and analysis. If more than one type of fluid is being used for peritoneal or other dialysis treatment, it may be useful to check the composition of each container, to insure that the proper containers have been procured and are connected correctly to the peritoneal dialysis machine.

Dialysis fluid may be used in more than one pass, i.e., hemodialysis fluid may be routed more than once through the dialyzer before it is filtered or purified and peritoneal dialysis fluid may also be used in multi-pass therapies. There is at present no easy way to monitor the composition of the fluid before the first pass, or after the first or second pass, short of taking a sample and sending it to a laboratory for analysis. Using a plurality of standard sensors at one or more points in the fluid circuits would be very expensive and would also occupy space that is not available at the bedside of the patient, whether in a home-care or even in an institutional-care setting.

SUMMARY

There are many embodiments of the present invention, in which MEMS sensors are used to sense and quantify analytes of interest in dialysis fluid and in water for use in dialysis fluid. The MEMS sensors are useful in dialysis fluid intended for both peritoneal dialysis and hemodialysis.

In a first embodiment of the present invention, a system for preparing dialysis fluid is provided. The system includes a first purification vessel which includes a purification medium for water, and a device for pumping or measuring the water. The system also includes a heater for heating the water and a mixing chamber configured for receiving water from the device and for mixing the water with a concentrate to form a fresh dialysis solution. A filter for filtering the fresh dialysis solution is provided, as well as a microelectromechanical systems (MEMS) sensor that is placed in fluid communication with an output from a vessel selected from the first purification vessel, the heater, the mixing chamber and the filter.

In a second embodiment of the present invention, a system for preparing dialysis fluid is provided. The system includes a first purification cartridge that includes a purification medium for water, and also includes a heater for heating water received from the first purification cartridge. The system also includes first and second pumps for pumping and metering first and second concentrates, and a mixing chamber configured for receiving the first and second concentrates from the first and second pumps and for mixing the first and second concentrates. The mixing chamber is used to mix the water with the first and second concentrates to form a fresh dialysis solution. The system further includes a filter for filtering the fresh dialysis solution, and a microelectromechanical systems (MEMS) sensor placed in fluid communication with an output of a vessel selected from the first purification vessel, the heater, the mixing chamber and the filter, wherein the MEMS sensor is suitable for sensing at least two substances in a stream selected from the group consisting of water from the first purification cartridge, the fresh dialysis solution and the filtered dialysis solution.

In a third embodiment of the invention, a method for preparing dialysis solution is provided. The method includes the steps of furnishing a supply of water and purifying the water in at least one pass through a purification medium. The method also includes the steps of heating the water and adding the water to at least one dialysis concentrate to form a dialysis solution. In addition, the method includes the steps of filtering the dialysis solution and sensing at least two characteristics of the water with a microelectromechanical systems (MEMS) sensor.

In a fourth embodiment of the invention, a method of preparing dialysis solution is disclosed. This method includes the steps of furnishing a supply of water and spent dialysate and purifying the water and the spent dialysate in at least one pass through a purification medium. The purification medium may be in one vessel or more than vessel, as described below. The method also includes the steps of heating the water and adding the water and at least one dialysis concentrate to form a dialysis solution. In addition, the method includes filtering the formed dialysis solution and sensing at least two characteristics of a stream selected from the group consisting of the water, the formed dialysis solution and the spent dialysis solution, using a microelectromechanical systems (MEMS) sensor.

In a fifth embodiment, a method of purifying dialysis solution is disclosed. The method includes the steps of furnishing a supply of spent dialysate and purifying the spent dialysate in at least one pass through a purification medium in a vessel to form a purified dialysate. The method also includes the steps of filtering the spent dialysate to form a filtered dialysate, and sensing at least two characteristics of a stream selected from the group consisting of the spent dialysate, the purified dialysate and the filtered dialysate. The characteristics are sensed with a microelectromechanical systems (MEMS) sensor.

Another embodiment is a method for performing dialysis. The method includes the steps of providing a dialysis machine and a supply of dialysis fluid and also includes the steps of sensing and determining a composition of the dialysis fluid with a MEMS sensor. The MEMS sensor is suitable for sensing and detecting at least two ions in the dialysis fluid. The method also includes the steps of performing dialysis on a patient using the dialysis fluid, and sensing and determining a composition of the dialysis fluid after the step of performing dialysis, using a MEMS sensor. Additionally, the method includes the steps of purifying the dialysis fluid after the step of performing dialysis, and sensing and determining a composition of the dialysis fluid after the step of purifying with a MEMS sensor. The method includes a step of reusing the dialysis fluid if the composition of the dialysis fluid after the step of purifying is suitable for dialysis.

Additional features and advantages are described herein, and will be apparent from the following Detailed Description and the figures.

DETAILED DESCRIPTION

Figure 1:
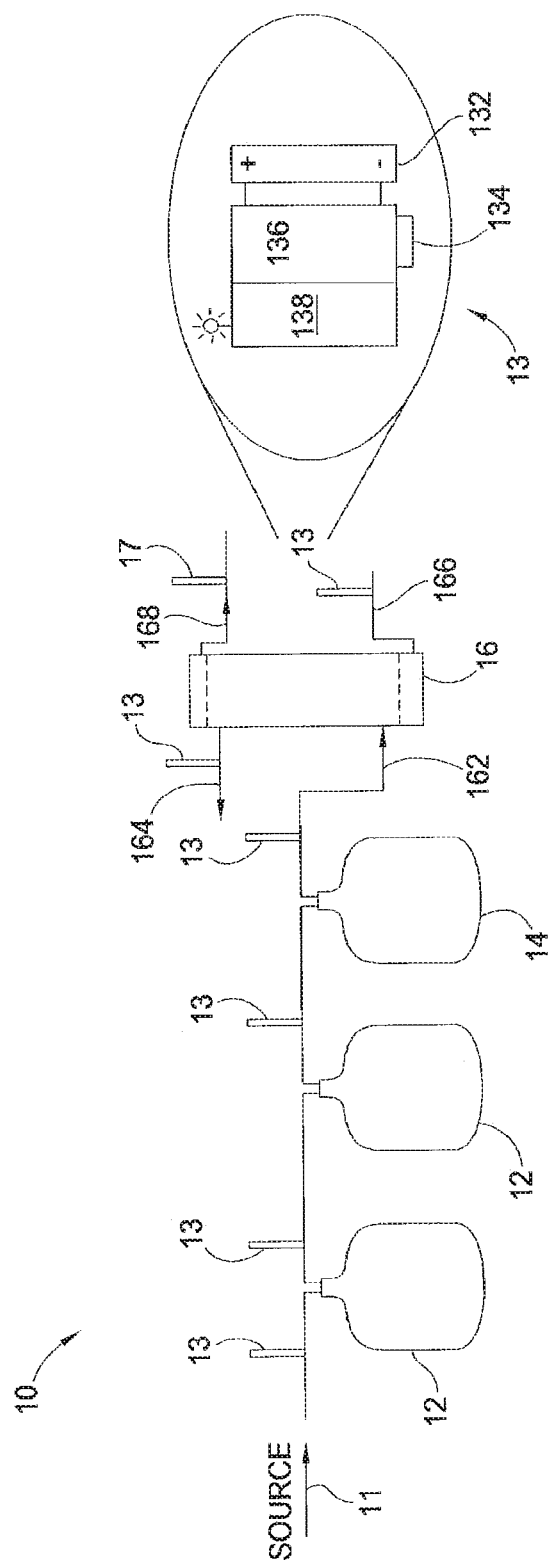
FIG. 1 is a schematic view of a first system for purifying water or spent dialysis solution before hemodialysis.

MEMS sensors are used in embodiments of the present invention to detect and quantify analytes of interest in dialysis fluids. MEMS sensors are capable of detecting numerous properties and species in a variety of aqueous fluids. These fluids include water, dialysis fluid, spent dialysis fluid and even blood. The properties include pH, conductivity, temperature, oxidation-reduction potential and total hardness. Species include ammonia or ammonium, total dissolved solids (TDS), carbonate, bicarbonate, calcium, magnesium, sodium, potassium, chloride and others.

A MEMS sensor includes a substrate with a plurality of electrode sensor elements adapted to measure relevant species of an aqueous analyte. The sensor elements include, for example, electrodes and selective membranes. These elements, together with any support circuitry required to drive the sensor element, make up the complete sensor. For example, the substrate can include a plurality of electrodes covered by ion-selective membranes and an amperometric sensor including a working electrode and a counter electrode. In one application, the substrate, including the sensor elements, is connected to an analyzer capable of calculating one or more desired properties, such as the disinfection index of a water sample. Optionally, the substrate includes additional sensor elements configured to measure additional species. These element may include an ammonia sensor, an oxygen sensor, or a sensor for a mutagenic species, such as an immunosensor or a DNA probe. Sensors may also be used to detect and quantify additional physical properties, such as temperature, conductivity and oxidation-reduction potential.

Exemplary sensors can be fabricated on silicon substrates. They may alternatively be fabricated on other types of substrates such as, for example, ceramic, glass, $SiO_2$, or plastic, using conventional processing techniques. Exemplary sensors can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components. These other sensor components may include sensing elements, one or more reference electrodes, or both. Conventional electronics processing techniques can be used to fabricate and interconnect such composite devices. These techniques are also described in U.S. Pat. Nos. 4,743,954 and 5,102,526, which are hereby incorporated herein by reference.

The sensors can utilize micro-array sensor chip technology on a silicon platform. For example, ion-selective electrode-based sensor elements can be implemented in a silicon-based embodiment, such as that as described by Brown, "Solid-state Liquid Chemical Sensors" (Miniaturized Analytical Devices Microsymposium, Chemistry Forum, 1998, pp. 120-126), the disclosure of which is hereby incorporated herein by reference. Alternative silicon-based sensor devices, and the manners in which such devices can be fabricated, are described in U.S. Pat. No. 4,743,954 ("Integrated Circuit for a Chemical-Selective Sensor with Voltage Output"), U.S. Pat. No. 5,102,526 ("Solid State Ion Sensor with Silicone Membrane"), and U.S. patent application Ser. No. 09/768,950 ("Micromachined Device for Receiving and Retaining at Least One Liquid Droplet, Method of Making the Device and Method of Using the Device"), the disclosures of which are hereby incorporated herein by reference. The chip platform can be based on other electrochemical solid state sensor technology that is well known in the art, as shown by Brown et al. in Sensors and Actuators B, vol. 64, June 2000, pp. 8-14, the disclosure of which is hereby incorporated herein by reference. The silicon chip incorporates a combination of chemically-selective sensors and physical measurements that work in concert to deliver chemical profiling information on a test sample as small as one drop, and which are also suitable for continuous, on-line sensing and monitoring of fluids.

As described in U.S. Pat. Appl. Publ. 20080109175 (filed Aug. 30, 2007, now abandoned), which is hereby incorporated herein by reference, sensors for use in systems disclosed herein can be fabricated using known lithographic, dispensing and screen printing techniques. These include conventional microelectronics processing techniques. These techniques can provide sensors having sensing elements with micro-sized features integrated at the chip level, and can be integrated with low-cost electronics, such as ASICs (application specific integrated circuits). Such sensors and electronics can be manufactured at low cost, thereby enabling wide distribution of such sensors for general use. The sensor may be a MEMS sensor as sold by Sensicore, Inc., Ann Arbor, Mich., U.S.A. These sensors use microelectromechanical systems (MEMS) technology, that is, very small devices with very small components. These sensors are described in numerous patents and patent publications from Sensicore, including U.S. Pat. Nos. 7,100,427; 7,104,115; 7,189,314; and 7,249,000, each of which is hereby incorporated by reference in its entirety and relied upon. These MEMS sensors are also described in numerous patents pending, including U.S. Pat. Appl. Publications: 20050251366 (filed May 7, 2004, now abandoned); 20060020427 (filed Aug. 9, 2005, now abandoned); 20060277977 (filed Aug. 23, 2006, now U.S. Pat. No. 7,367,222); 20070050157 (filed Jun. 9, 2006, now U.S. Pat. No. 7,424,399); 20070219728 (filed Nov. 16, 2006, now abandoned); and 20080109175 (filed Aug. 30, 2007, now abandoned), each of which is hereby incorporated by reference in its entirety and relied on.

The microelectromechanical system (MEMS) sensors may be used in many aspects of dialysis fluid preparation and processing to ensure patient safety, comfort, economy and convenience, as well as treatment efficacy. The economy and convenience arise from the use at home of the embodiments described below, as well as many other embodiments that are not described here, but will be obvious to those having skill in dialysis arts.

FIG. 1 illustrates a first embodiment of a system 10 for preparing fresh dialysis solution from spent dialysate using MEMS sensors to sense, measure, and report various characteristics of the dialysate. In this system, dialysis fluid enters from a source 11 of dialysis fluid, such as the effluent from a spent dialysate pump that forms part of a hemodialysis machine. FIG. 1 depicts a plurality of sensors 13, located at several points around the system 10. The intent is not to suggest that a sensor is needed at every point depicted, but rather to demonstrate the plurality of locations where a sensor may advantageously be placed.

Each sensor 13, as shown in the inset, includes a power source 132, such as a battery, a sensing element 134 with a working portion 136, and, optionally, a module 138 for remote communication, such as to a controller of the system. The power source may be furnished by electrical wiring from a controller of the hemodialysis machine, or from another power source, such as a convenience outlet or a modular power supply for a series of MEMS sensors.

Sensor element 134 is a MEMS sensor and working portion 136 includes the circuitry necessary to process signals from the sensor and convert them to useful information. These signals may be sent to a controller of the hemodialysis machine via wired connections, or the MEMS sensor may include a remote communications capability. In this embodiment, the signal processing circuitry and wireless transmitter or radio 138 are small and compact, and are easily placed into the sensor housing at the sensing site. One suitable remote communications module is a wireless module in accord with the ZigBee/IEEE 805.15.4 standard. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The modules are very small and are suitable for such remote applications. As noted, the sensor 13 optionally includes a power supply and may also include an ADC converter to convert analog data from the sensing element into digital data. The digital data is thus formatted, at least by the sensor, before transmission to the controller of the hemodialysis machine or other extracorporeal processing machine controller.

MEMS sensors include sensors which may be placed in-line between one vessel and a succeeding vessel, and also include sensors which may be placed within a vessel, such as a processing vessel or cartridge, or a storage vessel. Many MEMS sensors are capable of detecting many species of ions or contaminants, and some are also capable of sensing and relaying a temperature, pH (as in hydrogen or hydronium ion concentration), conductivity, total dissolved solids (TDS), and so forth.

Hemodialysis Applications

Returning to FIG. 1, system 10 includes a source 11 of water or spent dialysis fluid, with a MEMS sensor 13 placed at the source for monitoring characteristics of the incoming water or fluid. A first processing vessel 12, such as a bed of activated carbon or charcoal, is placed downstream of the source 11. The bed of activated carbon or charcoal is excellent for removing a number of contaminants, including small particles and also including chlorine, chloramines, and organics, among others. The bed of activated carbon or charcoal is relatively non-selective in the types of contaminants removed. If desired, a second processing vessel 12 or bed of activated carbon or charcoal may be used, with a second sensor 13 placed downstream of the second vessel. This will allow the user time to change beds, for instance, if a dialysis treatment is needed after the sensor for the first bed has indicated that the effluent is above an acceptable limit for a particular contaminant, such as chloramine, $\beta_2$-microglobulin, or creatinine.

After one or two beds of activated carbon or charcoal, another vessel 14 for purification of the water or spent dialysate may be used, with a fourth sensor downstream of vessel 14. This vessel may include any desired purification substance, and may include a single adsorbent or more than one layer of different adsorbents. Vessel 14 may include a layer of urease and zirconium phosphate for converting urea into ammonium ions and then removing the ammonium by forming ammonium phosphate. Alternatively, or in addition, there may be a layer of zirconium oxide for removing phosphates or sulfates. Vessel 14 may also include an ion exchange resin suitable for exchanging ions of waste substance for ions that are desirable in dialysis solutions, such as calcium or magnesium ions, and also bicarbonate or acetate ions. The ion exchange resin may include filtering beds of carbon or charcoal before or after, or before and after, the resin itself. These supplemental beds also help to purify the final product, whether water for making dialysate or refreshed dialysate for service to the patient.

In the embodiment of FIG. 1, once the rejuvenated dialysis fluid leaves vessel 14, it is routed to the dialysate side of a dialyzer 16, used for hemodialysis. A dialyzer may be compared to a shell-and-tube heat exchanger, with the dialysate on the shell side and the blood of the patient running through the tube side counter-current to the dialysis fluid. In this embodiment, the dialysis fluid enters through inlet port 162 and leaves through dialysis fluid outlet port 164, where an additional MEMS sensor may sense and measure a variety of species within the exiting dialysis fluid. Once the dialysis fluid leaves through outlet port 164, it may be disposed of or may be sent again to be filtered and purified for another pass.

The other side of the dialyzer is connected to the patient's blood. Blood enters through the inlet header 166, flows through many hundred or thousand tiny porous tubes, and then leaves through the outlet header 168. The tiny porous tubes allow water and toxic substances in the blood, such as creatinine and urea, to flow from the blood side to the dialysis solution side. In addition, electrolytes and bicarbonate buffer may flow from the dialysis solution side to the blood side. The cleansed blood is then sent to an air detector or air trap before returning to the patient. An additional sensor 13 may be used to check the composition of the incoming blood for contaminants or other species near inlet header 166. An additional sensor 17 may be used to check for contaminants or other species near outlet header 168. Sensor 17 may be tuned for different species than sensor 13, for example, measuring pH, phosphates or urea, may be very important to determine the condition of the cleansed blood as it is returned to the patient.

Figure 2:
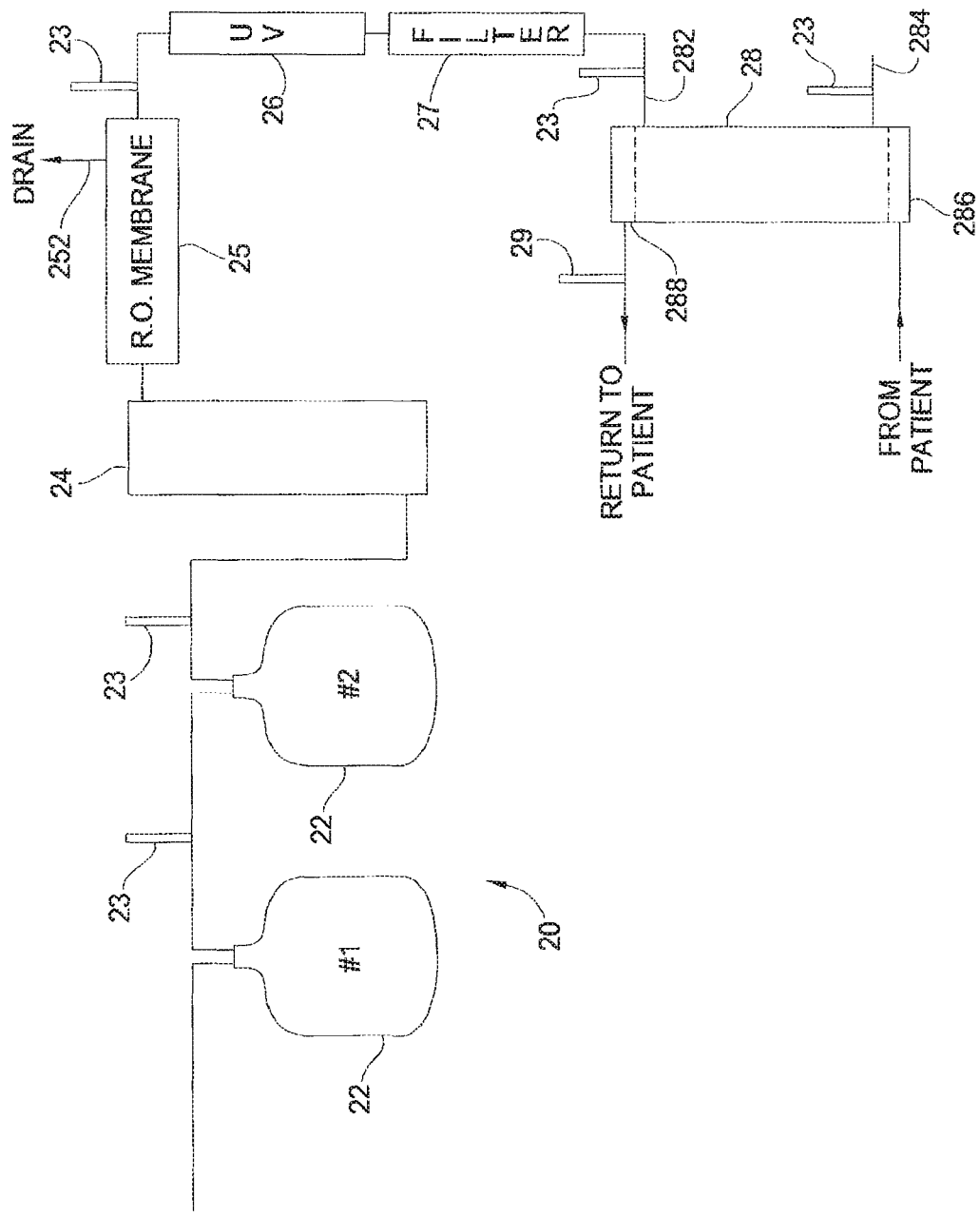
FIG. 2 is a schematic view of a second system for purifying water or spent dialysis solution before hemodialysis.

It is understood that other cleansing and purifying devices may be used to purify incoming water or to cleanse spent dialysate fluid for reuse. These alternatives include filters, such as small particle filters and even ultrafilters, such as submicron filters, for removing bacterial or endotoxin contaminants. A second embodiment of a system 20 that advantageously uses MEMS sensors is depicted in FIG. 2. System 20 includes first and second purifying vessels 22, which may be small cartridges rather than gallon-size vessels. A MEMS sensor 23, as described above, senses and measures levels of the desired contaminants or species, as described above.

In system 20, there is also an 5 micron filter 24 followed by a reverse-osmosis filter 25, with a waste outlet 252 to drain. The reverse-osmosis filter 27 may be equipped with a MEMS sensor 23 that includes a temperature sensor, for proper operation of the reverse-osmosis filter. The MEMS sensor may also include one or more sensors that monitor specific ions or substances, such as ammonia or ammonium, total dissolved solids (TDS), $Ca^{++}$, $Mg^{++}$, $Na^+$, $K^+$, $Cl^-$, and so forth. After reverse-osmosis, the system may include a UV-light generator 26, wherein the light generated is cidal to bacteria and other harmful microorganisms. Additionally, the light may be used to dissociate chloride ion from nitrogen atoms in chloramine molecules, thus removing chloramines from the water or dialysis fluid. Ultraviolet light for these applications is typically UV-C, with a wavelength from about 180-290 nm. Lamps with a wavelength of about 185 nm or about 254 nm are preferred. Without being bound to any particular theory, it is believed that UV light penetrates the outer cell walls of microorganisms, where it passes through the cell body, reaches the DNA and alters the genetic material, and is thus cidal to the microorganism. Other desired wavelengths may be used.

An ultrafilter 27 is placed downstream of the UV light generator, followed by the dialyzer. Dialyzer 28 has a dialysis fluid inlet 282 and a dialysis fluid outlet 284, each of which may also be equipped with a MEMS sensor 23. Dialyzer 28 has a blood inlet header 286 and a blood outlet header 288 opposite the inlet header. The composition of the blood at the outlet may be sensed and monitored by a MEMS sensor 29 that is tuned, as above, for a particular component or property of the blood that is important, such as pH, phosphate, or urea.

The patient or a caregiver may take special note of the sensor readings from sensor 29 and from the last sensor 23 at the dialysis fluid outlet 284. Readings of the composition or the state of the blood is important to gauge whether the dialysis treatment is working and whether dialysis should be continued as is or whether some modification to the patient's prescription may be needed, whether dialysis fluid, duration or frequency of the treatment, and so forth. Of course, a comparable result may also be achieved by analyzing the composition of the spent dialysis fluid, since the waste that leaves the patient's body must either remain in the dialyzer or enter the dialysis fluid. The condition of the spent dialysis fluid is thus important. If the fluid has toxic components within certain high ranges, it may be expedient not to re-use any part of the fluid and to instead replace it with fresh dialysis fluid. If the range is more reasonable, a user or caregiver may decide to recycle and refresh at least part of the spent fluid, rather than sending it to drain. The composition of the spent dialysate also provides information on the efficacy of the dialysis therapy, albeit not as precisely as monitoring the patient's blood. While not depicted in FIG. 2, it is understood that there may be one or more metering pumps or flow meters to control the flow of dialysis fluid to and from dialyzer 28 or any of the process vessels or cartridges upstream of dialyzer 28. It should be understood that many of the techniques and much of the equipment described above may be applicable to both hemodialysis and peritoneal dialysis applications.

Peritoneal Dialysis Applications

Figure 3:
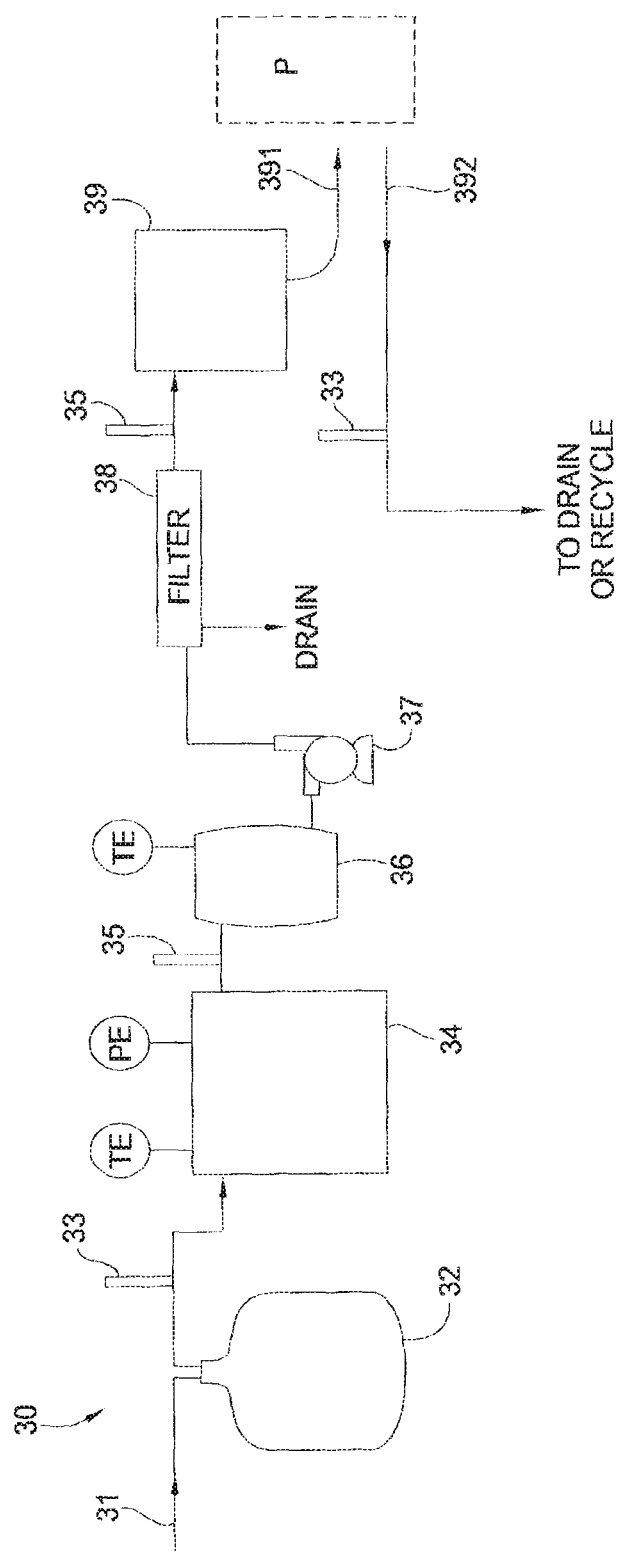
FIG. 3 is a schematic view of a third system for purifying water and preparing dialysis solution, directed more to peritoneal dialysis.

A system 30 designed for peritoneal dialysis is depicted in FIG. 3. System 30 accepts water or spent dialysate fluid from a source 31, such as a water tap or an outlet from a patient yielding spent dialysate. The system includes at least one vessel 32 for purifying the water or spent dialysate. In a manner similar to that described above for the other systems, first vessel 32 may include activated carbon or charcoal, or may include more than one layer for selectively or non-selectively adsorbing impurities or wastes from either water or from spent dialysis fluid. The system includes a MEMS sensor 33, as discussed above. In this system, the spent dialysis fluid or water is sent to a dialysis fluid preparation system 34, of which one embodiment is described below in FIG. 6.

In one example, the dialysis fluid preparation system may simply be a container with a known quantity of concentrate of known composition. For example, system 34 may be a flexible container with a known volume (liquid) or a known mass (solid) of a known concentrate for a single component dialysis solution, e.g., a dialysis lactate solution. A dialysis lactate solution typically contains electrolytes, lactate, and glucose. The water source 31 and necessary controls, such as a control valve in series with the water source of the vessel 32, are used to admit the proper amount of water to system 34, where the components are mixed and dissolved to form the desired solution. The amount of water or spent dialysate admitted may be measured, for example, by monitoring a positive-displacement pump for the fluid or water, or an accurate positive-displacement meter in series with the in-flow Alternatively, the amount of water or fluid can be controlled by weighing the mass admitted, e.g., by placing container 34 on a weigh scale, mass cell, or other device.

It is understood that dialysis solution preparation may include heating or pressurization, or both heating and pressurization, and hence at least one temperature sensor or temperature element and at least one pressure sensor or pressure element may be used in the dialysis fluid preparation. The resulting dialysis solution is checked at least once after its preparation by MEMS sensor 35.

In this embodiment, the fresh dialysis fluid is stored in at least one container 36 and its temperature is sensed and monitored by at least one temperature element or temperature sensor. When the dialysis fluid is needed, it is pumped via pump 37 through a filter 38, which routes the impurities to a drain and sends the purified filtrate to a peritoneal dialysis machine 39. The contents of the fluid may be checked by an additional MEMS sensor 35 at the input to the peritoneal dialysis machine. As is well known to those in peritoneal dialysis arts, the peritoneal dialysis machine may operate in one or more modes to route dialysis fluid to the peritoneum of the patient for a dwell period, or for a continuous flow-through mode, or other mode. The dialysis fluid may be routed to the patient P through the inlet lumen 391 of a two-lumen catheter, as shown. When the dwell time is reached, or if the flow-through is continuous, the dialysis fluid is routed from the patient through the outlet lumen 392 of a two lumen catheter. The make-up of the spent dialysis fluid returned from the patient may be checked by an additional MEMS sensor 33 for the parameters discussed above.

Figure 4:
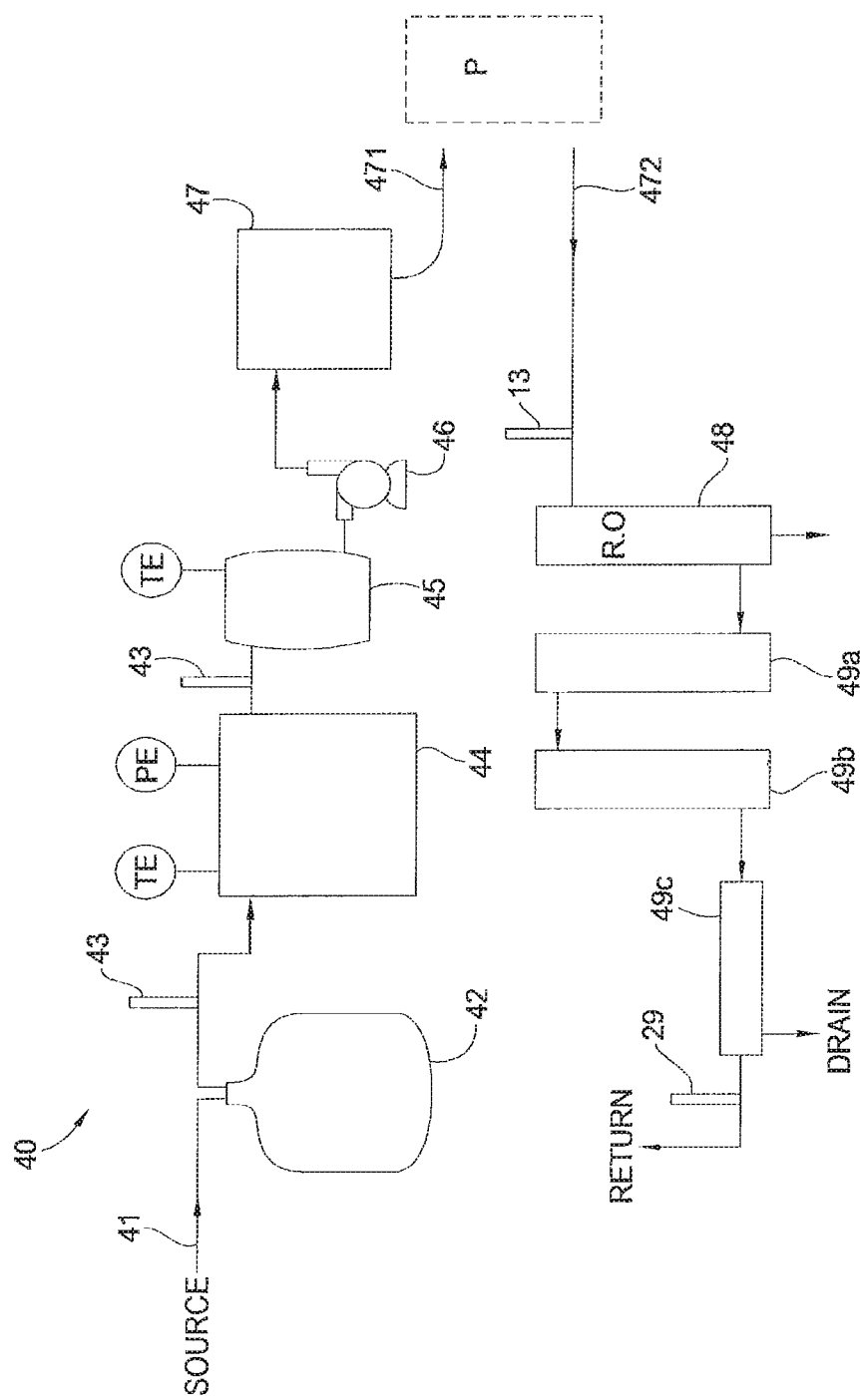
FIG. 4 is a schematic view of a system for purifying water and preparing dialysis solution, especially for peritoneal dialysis.

There are other embodiments that may advantageously use MEMS sensors for the preparation of dialysis solutions, including solutions for hemodialysis and for peritoneal dialysis. Another system directed more towards peritoneal dialysis is depicted in FIG. 4. System 40 includes a water source 41, which may be a municipal water source, or other water source, or may be a source of spent dialysate. A first filter or treatment vessel 42 is intended to remove impurities such as described above, the filter followed by a first MEMS sensor 43. In this embodiment, the purified water or dialysis fluid is then routed to a system 44 for producing dialysis fluid, one embodiment of which is depicted below in FIG. 6. As noted above, temperature and pressure elements may advantageously be used in preparation of dialysis fluid from concentrates. The composition of the resulting dialysis fluid is sensed and checked at a second MEMS sensor 43, as the dialysis fluid is routed to one or more storage containers 45, where the temperature may be monitored by one or more temperature elements to ensure safe storage.

When the dialysis fluid is needed, it is pumped by pump 46 to a peritoneal dialysis machine 47, and then to and from the patient by a catheter with two lumens, input lumen 471 and output lumen 472. In this embodiment, the spent dialysate is routed to a reverse osmosis filter 48, with the waste routed to a drain. In this embodiment, there are also first and second vessels or filters 49a, 49b, which may be used to remove contaminants, as described above, or may be used with ion exchange resins to remove contaminants and add desirable components. An electro-deionization process unit may also be used to remove ionic contaminants. An ultrafilter 49c is used to filter the solution and to route waste to the drain. Other embodiments may also be used. MEMS sensors 13, 29 may be used as indicated, such as after the dialysate is returned from the patient, and after the treatment vessels or filters, and the ultrafilter. MEMS sensors 13, 29 and 43 may be the same or may be tuned or capable of sensing different species, different ions, or different substances, as desired and as explained above.

Figure 5:
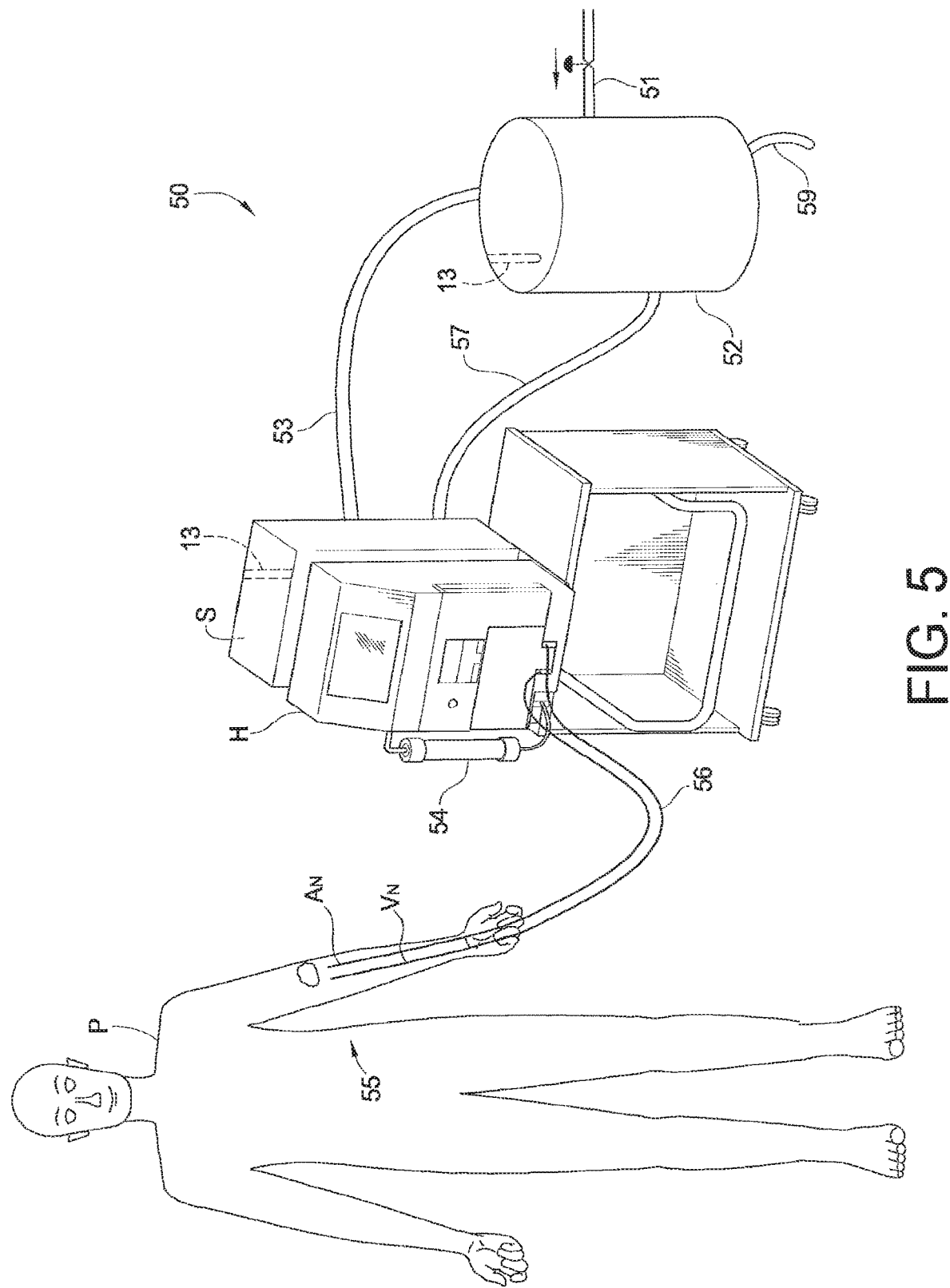
FIG. 5 is a perspective view of a hemodialysis machine with a system for treating, purifying, and reusing spent dialysate.

FIG. 5 depicts a home hemodialysis system 50 with a water or dialysate recycling system 52 as described above. System 50 includes an incoming city water tap 51 to a water or dialysate recycling system 52, which also includes a drain 59 for waste water. Fresh dialysis fluid is sent through tubing 53 to a storage container S adjacent hemodialysis machine H with dialyzer 54. As is well known to those with skill in dialysis arts, the patient P has a vascular access site 55 for an arterial needle $A_N$ and a venous needle $V_N$. The patient P is connected to the hemodialysis machine H via tubing 56. Spent dialysis fluid is returned to the recycling system 52 via tubing 57.

The MEMS sensors 13 described above may be used at several points in system 50. One or more sensors 13 may be deployed within the dialysate recycling system 52, for instance, to check on the incoming water from source 51 or the returned dialysate from tubing 57. Depending on the water or dialysis quality, a decision is made whether to send the returned dialysate to the drain 59 or to reuse the dialysate by cleaning, filtering, and replenishing the dialysate. A second MEMS sensor may be used to monitor the quality and composition of the dialysate sent to, or stored in, dialysis fluid storage container S. As a third example, another MEMS sensor 13 may be deployed within hemodialysis machine H to monitor the composition of the returned dialysate or species within the patient's blood. As discussed above, this sensor can help the patient or the caregiver determine whether the dialysis process is changing the appropriate parameters of the blood or the dialysis fluid, thus giving an indication of whether the therapy is working as effectively as desired.

Figure 6:
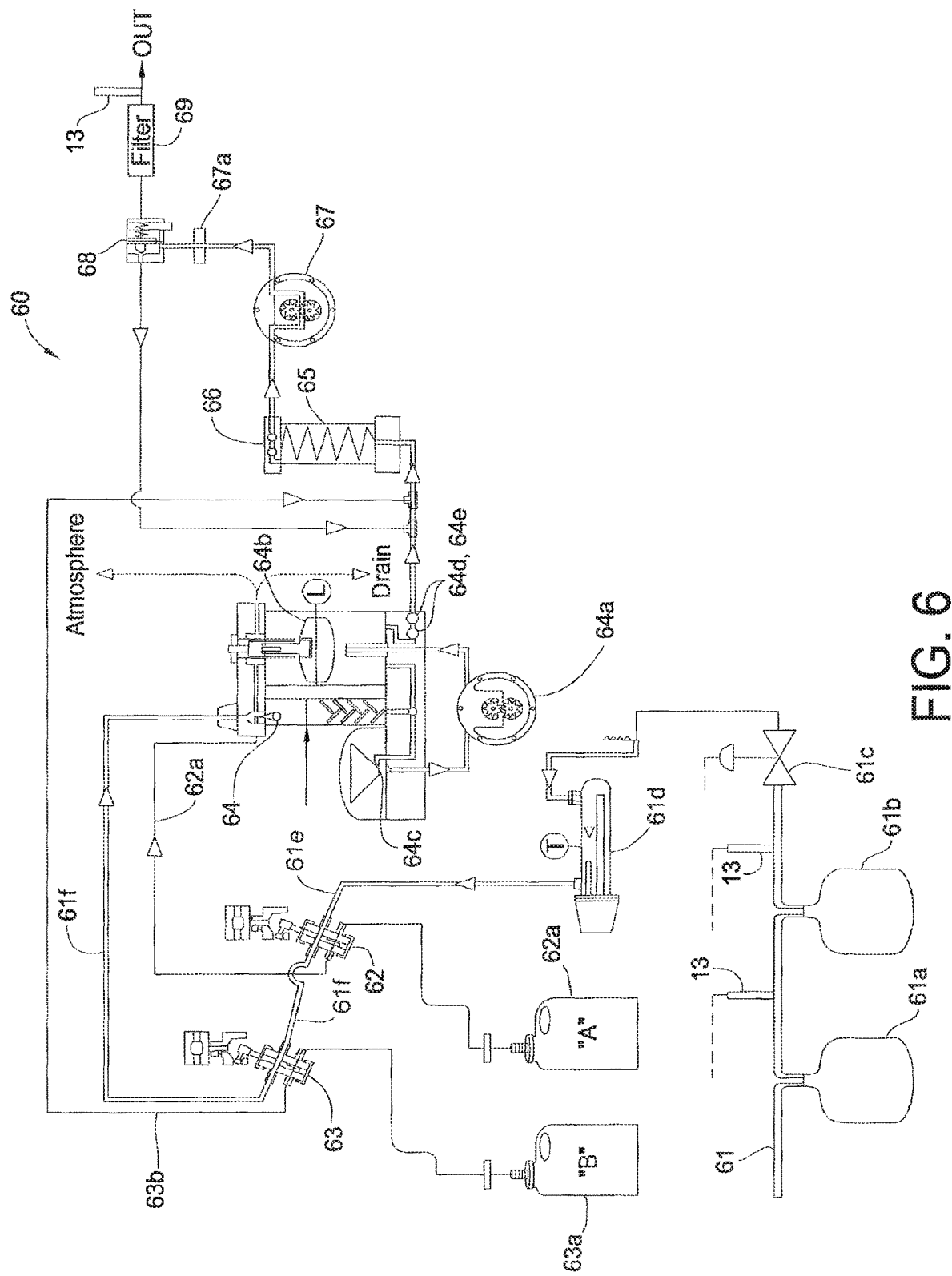
FIG. 6 is a schematic view of a system for preparing dialysis solution using MEMS sensors.

A system for preparing dialysis fluid from concentrate using make-up water or cleansed dialysis fluid is depicted in FIG. 6. One system 60 for producing dialysate is depicted in FIG. 6. System 60 receives water from water source 61 and passes the water through one or more purification vessels 61a, 61b, as described above. MEMS sensors 13 are used to sense and report the sensed quantities of impurities or other components of the water as it flows from the first and second vessels. The water passes through control valve 61c and is heated, if desired, using in-line heater 61d. The heated water flows through lines 61e, 61f to A and B concentrate pumps 62, 63, for pumping concentrate respectively from reservoirs 62a, 63a. The pumps are positive displacement pumps, such as gear pumps, vane pumps, or piston pumps, to pump precise amounts of A or B concentrate. One embodiment uses small ceramic piston pumps, available from Fluid Metering, Inc., Long Island, N.Y., U.S.A. Other pumps may be used. Other embodiments use proportioning or ratiometric pumps, whose flow of A or B concentrate may be set, and which thereafter pump A and B concentrate in a ratio proportional to the water metered out by the pumps.

Other than volumetric ratio, the pumps may be controlled by a feedback loop that includes a MEMS conductivity monitor. The concentrate pump is sped up if the conductivity at the conductivity sensor 64e is too low or is slowed if the conductivity at the probe is too high. Since the characteristic volumes of the concentrate pumps are known, there are limits on the amount of cycling needed to produce a stable dialysis solution. A controller for the system keeps track of the amounts of concentrate pumped, and also keeps track of the amount of incoming water and A concentrate that is pumped, thus keeping precisely proportioned flows.

In this embodiment, A concentrate pump 62 pumps A concentrate to mixing vessel 64 through line 62a, the vessel not filled but retaining an air gap at its top, while the correct ratio of water also flows to the vessel through line 61f. After the water and the A concentrate are mixed, the mixture is deaerated by spraying using precision metering pump 64a, nozzle 64c, and air trap 64b. Other embodiments such as a simple restriction creating a starved intake to pump 64a, could be substituted for the sprayer to remove the air from the solution. The mixture is monitored by temperature sensor 64d and MEMS conductivity sensor 64e. Vessel 64 includes a level sensor L. The deaerated acid mixture is then sent to the B mix chamber 65, where B concentrate from the B concentrate pump through line 63b is added, in this case in-line.

The B mix chamber 65 is equipped with a second MEMS sensor 66 to monitor the composition of the finished dialysis solution. This sensor can check the conductivity of the finished solution, and may also check other parameters or qualities of the solution. For example, a WaterPoint™ 870 Sensor, from Sensicore, Inc., may be used to check several parameters, including conductivity, pH, temperature, total dissolved solids (TDS, based on sodium ions), calcium, magnesium, total hardness, carbonate alkalinity, and other parameters. Many of these are very useful to a patient or to a caregiver preparing dialysis solution, since these measurements are directly related to the quality and make-up of the dialysis solution. As a check, this MEMS sensor can also sense and report general water quality, such as the concentrations of total and free ammonia (related to urea in the dialysate), chlorine, and chloramines. Other embodiments may use more than two concentrates, and the system may be changed to use a separate pump to pull the proper amount from each container of concentrate. Any of these systems may thus prepare a customized solution or prescription for each patient. The MEMS sensors may be used to monitor and control the process, as well as the final product, in any of these embodiments.

The dialysis solution is then pumped by supply pump 67 through filter 67a, to remove particles larger than 150 micrometers. Control valve 68 controls the flow (e.g., pressure) of dialysis solution from system 60. If the correct level of continuity has not been achieved, the freshly-prepared dialysis solution may be recycled as desired through the filter and the mixing chamber, as shown, until the proper mixing and purity has been achieved. The dialysis solution can then be pumped through a final filter, endotoxin filter 69, and checked by final MEMS sensor 13 after the filter, on its way to a storage container or for use. The endotoxin filter is intended to remove bacteria, such as *E. coli* and *P. aeruginosa*, as well as endotoxins. This filter could be an ultrafilter such as those made by Medica SRL, Mirandola, Italy, or from Nipro Corp., Osaka, Japan.

The process described above is only one method for preparing a dialysis solution. Other dialysis solutions may be used, including those requiring an osmotic agent, such as a small amount of dextrose, glucose, sodium or potassium polyacrylate, or mixtures of these, or other components. These solutions are prepared in generally similar ways, some embodiments using powders, some using concentrates, some using solutions. Any such embodiments, including MEMS sensors, are intended to fall within the scope of the present invention. Embodiments using powders may require a conventional stirred-tank vessel, or vessel suitable for mixing powders using a stirrer or using flow, often turbulent flow, to insure a good mixing. For home use, this may be any suitable mixer capable of maintaining and preserving sterility, when used with the MEMS sensors described above.

In addition to the MEMS sensors described above, other MEMS sensors are presently in development and testing. These include MEMS sensors that are capable of sensing and quantifying organic materials. These sensors work in the same manner as the other MEMS sensors, but operate by detecting analytes that are associated with an organic substance rather than an inorganic ion, such as ammonium or chlorine. These MEMS sensors are, or will be, capable of sensing total organic carbon (TOC), and also specific substances, such as urea, creatinine, $\beta_2$-microglobulin, heparin, and glucose or other sugar or osmotic agent in the dialysis fluid. MEMS sensors could also be used to detect levels of bacteria, endotoxins, and viruses in the water or spent dialysis fluid. In addition, MEMS sensors may be used to detect analytes of interest in the blood, such as proteins in general, including albumin, free hemoglobin and hematocrit.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A fluid preparation apparatus for a renal failure treatment comprising:
   an inlet configured to receive water from a water source;
   a fluid line fluidly connected to the inlet;
   a first concentrate pump fluidly connected to the fluid line at a first mixing point, the first concentrate pump configured to pump concentrate from a first concentrate container to mix with the water beginning at the first mixing point to form a first fluid mixture;
   a second concentrate pump fluidly connected to the fluid line at a second mixing point, downstream from the first mixing point, the second concentrate pump configured to pump concentrate from a second concentrate container to mix with the first fluid mixture beginning at the second mixing point to form a second fluid mixture;
   a microelectromechanical systems ("MEMS") sensor located downstream from the second mixing point and configured to measure a composition characteristic of the second fluid mixture;
   a valve located downstream from the MEMS sensor; and
   at least one controller operably coupled to the first concentrate pump, the second concentrate pump, the valve, and the MEMS sensor, the at least one controller configured to
      receive at least one composition characteristic value from the MEMS sensor,
      determine whether a pumping speed of the first concentrate pump is to be adjusted based on the at least one composition characteristic value,
      determine whether a pumping speed of the second concentrate pump is to be adjusted based on the at least one composition characteristic value,
      adjust the pumping speed of at least one of the first concentrate pump or the second concentrate pump based on the at least one composition characteristic value, so that the second fluid mixture forms a solution suitable for the renal failure treatment,
      when the at least one composition characteristic value does not indicate that the second fluid mixture is suitable for renal failure therapy, (i) adjust the pumping speed of at least one of the first or the second concentrate pump to produce a new second fluid mixture, and (ii) cause the valve to route the second fluid mixture to a point located between the first mixing point and the second mixing point for generating the new second fluid mixture, and
      cause the valve to route the second fluid mixture or the new second fluid mixture for the renal failure treatment when the at least one composition characteristic value indicates that the second fluid mixture or the new second fluid mixture is suitable for the renal failure treatment.

2. The fluid preparation apparatus of claim 1, wherein the MEMS sensor is a second MEMS sensor and the composition characteristic is a second composition characteristic, the apparatus further including a first MEMS sensor located between the first mixing point and the second mixing point and configured to measure a first composition characteristic of the first fluid mixture.

3. The fluid preparation apparatus of claim 2, wherein the at least one controller is operably coupled to the first MEMS sensor, receives at least one first composition characteristic value from the first MEMS sensor, and adjusts the pumping speed of the first concentrate pump based on the at least one first composition characteristic value.

4. The fluid preparation apparatus of claim 1, further comprising a first mixing chamber located at the first mixing point, the first mixing chamber configured to enable the water to mix with the concentrate from the first concentrate container.

5. The fluid preparation apparatus of claim 4, further comprising a second mixing chamber located at the second mixing point, the second mixing chamber configured to enable the water to mix with the first fluid mixture.

6. The fluid preparation apparatus of claim 1, further comprising a temperature sensor located adjacent to the MEMS sensor, the temperature sensor configured to transmit at least one temperature value of the second fluid mixture to the at least one controller.

7. The fluid preparation apparatus of claim 6, further comprising a heater fluidly coupled to the fluid line and operably connected to the at least one controller, the heater configured to heat at least one of the water, the first fluid mixture, or the second fluid mixture,
   wherein the at least one controller transmits a signal to control the heater based on the at least one temperature value.

8. The fluid preparation apparatus of claim 1, wherein the composition characteristic is at least one of a conductivity, a pH, a temperature, a total dissolved solids, a calcium level, a magnesium level, a total hardness, or a carbonate alkalinity.

9. The fluid preparation apparatus of claim 1, wherein the MEMS sensor includes a sensor element having a selective membrane that provides for measurement of the composition characteristic of the second fluid mixture.

10. The fluid preparation apparatus of claim 1, wherein the fluid line is a to-patient fluid line and the MEMS sensor is a first MEMS sensor, the apparatus further comprising:
    a patient outlet line positioned to receive used dialysate from a patient; and
    a second MEMS sensor provided in the patient outlet line to measure a composition characteristic of the used dialysate.

11. The fluid preparation apparatus of claim 10, wherein the at least one controller is operably connected to the second MEMS sensor and configured to (i) route the used dialysate to a drain line if a value of the composition characteristic of the used dialysate indicates that the used dialysate is not reusable, and (ii) route the used dialysate to the fluid line before the first mixing point for reuse if at least one composition characteristic value of the used dialysate indicates that the used dialysate is reusable.

12. The fluid preparation apparatus of claim 10, wherein the composition characteristic of the used dialysate is at least one of a conductivity, a pH, a temperature, a total dissolved solids, a calcium level, a magnesium level, a total hardness, or a carbonate alkalinity.

13. A fluid preparation apparatus for a renal failure treatment comprising:
   an inlet configured to receive water from a water source;
   a to-patient fluid line fluidly connected to the inlet;
   a concentrate pump fluidly connected to the fluid line at a mixing point, the concentrate pump configured to pump concentrate from a concentrate container to mix with the water at the mixing point to form a fluid mixture;
   an outlet line fluidly connected to the fluid line downstream of the concentrate pump, the outlet line configured to provide the fluid mixture as a prepared solution for the renal failure treatment;
   a patient outlet line positioned to receive used dialysate from a patient;
   a microelectromechanical systems ("MEMS") sensor positioned at the patient outlet line to measure a composition characteristic of the used dialysate;
   a valve located downstream from the MEMS sensor; and
   at least one controller operably coupled to the concentrate pump, the valve, and the MEMS sensor, the at least one controller configured to
      receive at least one composition characteristic value from the MEMS sensor, and
      (i) adjust a pumping speed of the concentrate pump based on the at least one composition characteristic value, (ii) route the used dialysate to a drain line if the at least one composition characteristic value indicates that the used dialysate is not reusable, and (iii) cause the valve to route the used dialysate to the to-patient fluid line before the mixing point for reuse if the at least one composition characteristic value indicates that the used dialysate is reusable.

14. The fluid preparation apparatus of claim 13, wherein the composition characteristic is at least one of a conductivity, a pH, a temperature, a total dissolved solids, a calcium level, a magnesium level, a total hardness, or a carbonate alkalinity.

15. The fluid preparation apparatus of claim 13,
   wherein the at least one controller is configured to cause the valve to route the used dialysate to the drain line if the at least one composition characteristic value indicates that the used dialysate is not reusable.

16. A fluid preparation apparatus for a renal failure treatment comprising:
   an inlet configured to receive water from a water source;
   a fluid line fluidly connected to the inlet;
   a first concentrate container fluidly connected to the fluid line at a first mixing point, the first concentrate container configured to hold a first concentrate to mix with the water at the first mixing point to form a first fluid mixture;
   a first microelectromechanical systems ("MEMS") sensor located downstream from the first mixing point and configured to measure a first composition characteristic of the first fluid mixture;
   a second concentrate container fluidly connected to the fluid line at a second mixing point, downstream from the first mixing point, the second concentrate container configured to hold a second concentrate to mix with the first fluid mixture at the second mixing point to form a second fluid mixture;
   a second MEMS sensor located downstream from the second mixing point and configured to measure a second composition characteristic of the second fluid mixture;
   an outlet line fluidly connected to the fluid line downstream of the second MEMS sensor, the outlet line configured to carry the second fluid mixture;
   a valve located between the second MEMS sensor and the outlet line; and
   at least one controller operably coupled to a first concentrate pump, a second concentrate pump, the valve, the first MEMS sensor, and the second MEMS sensor, the at least one controller configured to
      receive at least one first composition characteristic value from the first MEMS sensor and at least one second composition characteristic value from the second MEMS sensor,
      determine whether a pumping speed of the first concentrate pump is to be adjusted based on at least one of the at least one first composition characteristic value or the at least one second composition characteristic value,
      determine whether a pumping speed of the second concentrate pump is to be adjusted based on at least one of the at least one first composition characteristic value or the at least one second composition characteristic value,
      adjust the pumping speed of at least one of the first concentrate pump or the second concentrate pump based on at least one of the at least one first composition characteristic value or the at least one second composition characteristic value, so that the second fluid mixture is made suitable for the renal failure treatment,
      when the at least one second composition characteristic value does not indicate that the second fluid mixture is suitable for the renal failure treatment, (i) adjust the pumping speed of at least one of the first or the second concentrate pump to produce a new second fluid mixture, and (ii) cause the valve to route the second fluid mixture to a point located between the first mixing point and the second mixing point for generating the new second fluid mixture, and
      cause the valve to route the second fluid mixture or the new second fluid mixture to the outlet line when the at least one second composition characteristic value indicates that the second fluid mixture or the new second fluid mixture is suitable for the renal failure treatment.

17. The fluid preparation apparatus of claim 16, wherein the first composition characteristic is the same as the second composition characteristic.

18. The fluid preparation apparatus of claim 16, wherein at least one of the first MEMS sensor or the second MEMS sensor is configured to measure at least one of a conductivity, a pH, a temperature, a total dissolved solids, a calcium level, a magnesium level, a total hardness, or a carbonate alkalinity.

19. The fluid preparation apparatus of claim 16, which is provided as part of a renal failure treatment machine.

* * * * *